United States Patent [19]

Fujino

[11] Patent Number: 4,691,030

[45] Date of Patent: Sep. 1, 1987

[54] PROCESS FOR PREPARATION OF ALKENYLSUCCINIC ANHYDRIDES

[75] Inventor: Kiyoharu Fujino, Yokkaichi, Japan

[73] Assignee: Mitsubishi Monsanto Chemical Company, Tokyo, Japan

[21] Appl. No.: 808,885

[22] Filed: Dec. 13, 1985

[30] Foreign Application Priority Data

Dec. 19, 1984 [JP] Japan ................................. 59-267889

[51] Int. Cl.$^4$ ........................................... C07D 307/60
[52] U.S. Cl. .................................................. 549/255
[58] Field of Search ......................... 549/255; 562/595

[56] References Cited

U.S. PATENT DOCUMENTS 4,431,826  2/1984  Sweeney ............................. 549/255

FOREIGN PATENT DOCUMENTS

F 10267  9/1956  Fed. Rep. of Germany ...... 549/255

OTHER PUBLICATIONS

Mantell, Adsorption, McGraw-Hill, pp. 44–49, 66–69, (1951).

Patterson, A. German-English Dictionary for Chemists, 3rd. Ed., John Wiley p. 75 (1950).

Primary Examiner—Henry R. Jiles
Assistant Examiner—Bernard I. Dentz
Attorney, Agent, or Firm—Burgess, Ryan and Wayne

[57] ABSTRACT

An alkenylsuccinic anhydride having a high quality is obtained at a low temperature in a high yield by subjecting an olefin having 2 to 90 carbon atoms and maleic anhydride to addition reaction under heating in the presence of a solid acid/base catalyst.

4 Claims, No Drawings

PROCESS FOR PREPARATION OF ALKENYLSUCCINIC ANHYDRIDES

BACKGROUND OF THE INVENTION

(1) Field of the Invention

The present invention relates to a process for the preparation of alkenylsuccinic anhydrides. More particularly, it relates to a process for the preparation of alkenylsuccinic anhydrides, in which formation of decomposition products of maleic acid or by-products having a high molecular weight by polycondensation is controlled and an alkenylsuccinic anhydride having a high quality can be prepared at a low temperature in a high yield.

(2) Description of the Related Art

Alkenylsuccinic anhydrides have been used as neutral sizing agents for paper, additives for lubricating oils and fuel oils for internal combustion engines, dispersants for lacquers, plasticizers, and intermediates for various chemical products. Recently, these anhydrides have become widely used as curing agents for epoxy resins, modifiers for alkyd resins, modifiers for phenolic resins, plasticizers for natural rubbers, synthetic rubbers, and thermoplastic resins such as polyvinyl chloride, dispersants, rust-preventing agents, grease, and spreaders for printing inks.

An alkenylsuccinic anhydride can be easily prepared by subjecting an olefin and maleic anhydride to an ene-addition reaction at a high temperature of 180° C. to 250° C. However, since the thermal reaction is carried out at a high temperature, discoloration of the product is extreme, and in many cases, by-products having a high molecular weight, sludges, tars and other undesirable by-products are formed by decomposition and polycondensation of the starting material and these by-products are incorporated in the product, resulting in an increase of the viscosity or gelation. Therefore, it is ordinarily necessary to subject the reaction product to distillation. Moreover, it is necessary to remove sludges or tars adhering to or left in the reaction vessel by washing or other means.

Various improvements for solving these problems have been proposed. For example, there can be mentioned processes disclosed in Japanese Examined Patent Publications No. 50-33,720, No. 53-2,678, No. 53-1,799, No. 52,-23,668, No. 52-39,674, and No. 52-48,639 and Japanese Unexamined Patent Publications No. 57-35,580 and No. 57-3,558. However, from the results of experiments made by us, it has been found that all of the foregoing defects cannot be completely eliminated by these improved processes.

SUMMARY OF THE INVENTION

It is a primary object of the present invention to provide a process for the preparation of alkenylsuccinic anhydrides, in which the formation of by-products having a high molecular weight, sludges, and tar-like products by decomposition and polycondensation of the starting material is controlled and an alkenylsuccinic anhydride having a high quality can be obtained at a low temperature in a high yield.

In accordance with the present invention, there is provided a process for the preparation of alkenylsuccinic anhydrides, which comprises subjecting an olefin having 2 to 90 carbon atoms and maleic anhydride to addition reaction under heating in the presence of a solid acid/base catalyst.

Olefins having 2 to 90 carbon atoms are used as the olefin ingredient in the present invention. These olefins include olefins having an even number of carbon atoms, obtained by oligomerization of ethylene, such as 1-olefine having 8, 10, 12, 14, 16, 18 or 20 carbon atoms and mixtures thereof; internal olefins formed by isomerizing 1-olefins; mixtures of trimer, tetramer, pentamer, and other oligomers inclusive of up to triacontamer, obtained by oligomerization of isopropylene; mixtures of dimer, trimer, tetramer, pentamer, and other oligomers inclusive of up to docosamer, obtained by oligomerization of isobutylene; and olefins obtained by dehydrochlorination of chlorinated paraffin.

The kind of the olefin used is appropriately selected depending upon the intended use of the alkenylsuccinic anhydride prepared by the present invention. For example, when the product is to be used as a solid wax, a 1-olefin is preferably selected, and when the product is to be used as a neutral sizing agent for paper, an internal olefin prepared by isomerizing a 1-olefin is preferably used. Furthermore, when the product is to be used for a printing ink or a lacquer, a low polymer (oligomer) such as a dimer, trimer, tetramer or pentamer of isopropylene or isobutylene is preferably used. When the product is to be used as a rust-preventing agent or dispersant in the field of petroleum and lubricants, preferably a low polymer is used such as a tetramer to triacontamer of isopropylene or a low polymer such as a trimer to decosamer of isobutylene.

As the solid acid/base catalyst used in the present invention, there can be mentioned silica/titania, silica/alumina, silica/titania/alumina, silica/titania/iron oxide, silica/alumina/iron oxide, alumina/iron oxide, silica/iron oxide, silica/alumina/magnesia, silica/alumina/calcium oxide, silica/titania/magnesia, and an alkali metal or alkaline earth metal aluminosilicate. In these solid catalysts, the compositions are not particularly limited. When an alkali metal or alkaline earth metal or an oxide thereof is contained as the active ingredient, it is preferred that the content of the active ingredient should not exceed the neutralization point of the solid acid. These solid acid/base catalysts may be used singly or in the form of mixtures of two or more thereof.

The solid acid/base catalyst may be prepared according to various known processes such as the homogeneous precipitation process, the impregnation process, and the gas phase synthesis process. According to the homogeneous precipitation process, a precipitate is formed from a homogeneous solution according to Weimarn's formula. According to the impregnation process, a commercially available molded catalyst carrier of silica, alumina or silica/alumina is impregnated with an aqueous solution of a salt containing a catalytic active component by competitive absorption or the like, and after drying, the impregnated salt is activated by thermal decomposition. According to the gas phase synthesis process, fine powders of oxides are formed by gas phase reaction. Furthermore, there may be adopted a process in which fine powders are mixed and the mixture is compression-molded.

It is preferred that the amount of the catalyst used be 0.001 to 5% by weight, more preferably 0.05 to 1% by weight, based on the weight of the olefin.

In the process of the present invention wherein the olefin is reacted with maleic anhydride, it is preferred that maleic anhydride be used in an amount of 0.5 to 1.2 moles per mole of the olefin. If the olefin/maleic anhydride molar ratio is too high, the amount of the unreacted olefin is inevitably increased and the cost increases due to the need for recovery of the unreacted olefin. If the above molar ratio is too low, the proportion of maleic anhydride decomposed is increased, and the probability of the addition of at least two moles of maleic anhydride to one mole of the olefin is increased, resulting in the formation of tar-like products, discoloration, gelation, and an increase in the viscosity of the product.

Generally, in the case of a branched olefin, addition reaction with maleic anhydride is not so easily caused as in the case of a linear olefin, and the probability of the addition of at least two moles of maleic anhydride to one mole of the olefin is larger than in the case of a linear olefin. Furthermore, in the case of a branched olefin, decomposition or copolymerization of maleic anhydride is readily caused, and if such a reaction takes place, the viscosity of the product is increased. On the other hand, in the case of a linear olefin, addition reaction with maleic anhydride is readily advanced even at a low temperature, as compared with the case of a branched olefin, and a 1:1 molar ratio adduct of the olefin and maleic anhydride is easily obtained. Among linear olefins, 1-olefins have an excellent reactivity.

Where the molecular weight of the starting olefin is high, it is preferred that reaction be carried out at an olefin/maleic anhydride molar ratio of at least 1. If this molar ratio is lower than 1, especially lower than 0.83, the content of succinic anhydride in one mole of the reaction product is undesirably increased.

In preparing the intended product according to the process of the present invention, the starting olefin and maleic anhydride are charged in a reaction vessel, the inner atmosphere of which is substituted in advance by an inert gas such as nitrogen, and the solid acid/base catalyst is then added in the reaction vessel. Alternatively, the olefin and solid acid/base catalyst are first charged in the reaction vessel and maleic anhydride is then added in the reaction vessel. Thus, the starting materials and catalyst are charged in the reaction vessel, and while the contents in the reaction vessel are being stirred, the temperature is elevated to 150° C. to 250° C. to effect the reaction over a period of 2 to 15 hours, to complete the addition reaction. It is preferred that the addition reaction be conducted at 150° C. to 200° C. until the conversion reaches 95%. If the attained conversion is low, it is preferred that the temperature be elevated to 230° C. to 250° C. at the terminal stage of the reaction to increase the conversion to 95% or higher.

After the termination of the reaction, the unreacted olefin is recovered under a reduced pressure, and the solid acid/base catalyst is removed by filtration or centrifugal separation.

The thus-obtained alkenylsuccinic anhydride can be widely used as a neutral sizing agent for paper, an additive for a lubricating oil or fuel oil for an internal combustion engine, a dispersant for a lacquer, a curing agent for an epoxy resin, a modifier for an alkyd resin, a modifier for a phenolic resin, a plasticizer for a thermoplastic resin, a rust-preventing agent, a grease, and a developing agent for a printing ink.

The following prominent effects can be attained according to the present invention, and therefore, the industrial utilization value of the present invention is very high.

(1) In the process of the present invention, since the solid acid/base catalyst is used, the conversion can be increased even at a low temperature, the reaction time can be shortened, and the yield can be improved.

(2) In the process of the present invention, the formation of by-products having a high molecular weight, sludges, and tars by decomposition and polycondensation of the starting material is controlled, and therefore, problems such as discoloration of the reaction product, increase of the viscosity of the reaction product, and the necessity for washing of the reaction vessel do not arise and the operation efficiency is improved, with the result that the intended product having a high quality can be prepared industrially advantageously.

The present invention will now be described in detail with reference to the following examples that by no means limit the scope of the invention.

EXAMPLE 1

(Preparation of Catalyst)

Water glass was mixed with an aqueous solution of aluminum sulfate so that the Si/Al molar ratio was 1/1, and 10% aqueous ammonia was added to the mixture to form a precipitate. After addition of a sufficient amount of aqueous ammonia, the precipitate was recovered by filtration, washed with water, and subjected to centrifugal dehydration to recover a dehydrated cake. Then, a 20% aqueous solution of iron oxalate was added to the dehydrated cake so that the Si/Al/Fe elementary ratio was 1/1/0.1. The mixture was air-dried, calcined at 350° C. for 3 hours and at 450° C. for 1 hour, transferred to a dessicator, and gradually cooled to obtain a silica/alumina/iron oxide catalyst [$SiO_2$/$Al_2O_3$/($Fe_2O_3$. $Fe_3O_4$)], in which the Si/Al/Fe elementary ratio was 1/1/0.1.

(Addition Reaction)

A pressure-resistant closed vessel having a capacity of 5 liters and provided with a stirrer was charged with 2.7 kg of a 1-olefin having 16 carbon atoms (Dialene AO-16 supplied by Mitsubishi Chem. Ind. Ltd.), 5 g of the catalyst obtained by the above method, and 0.98 kg of maleic anhydride, and the inside atmosphere of the reaction vessel was substituted by nitrogen gas.

Then, the inner temperature was elevated to 190° C. while the contents in the vessel were stirred, and this temperature was maintained for 2 hours. Subsequently, the temperature was elevated to 210° C. and the addition reaction was continued for 2 hours at this temperature.

The unreacted substances were recovered under a reduced pressure (50 to 10 Torr), and 3.2 kg of the intended alkenylsuccinic anhydride (hereinafter referred to as "ASA") was obtained. The conversion of maleic anhydride was 98%.

The reaction product was transparent and had a light yellow color. The presence of a sludge or tar-like by-product on the inner wall of the reaction vessel was not observed.

COMPARATIVE EXAMPLE 1

The addition reaction was carried out in the same manner as described in Example 1 except that the catalyst was not added.

The sum of the unreacted olefin and maleic anhydride recovered under a reduced pressure was 1.0 kg, and the amount of the obtained ASA was 2.6 kg.

The ASA had a dark brown color, and because of black sludge floating in the obtained ASA, the product was opaque. A small amount of a black tar formed during the addition reaction adhered to the gas/liquid interface on the inner wall of the reaction vessel.

EXAMPLE 2

(Preparation of Catalyst)

Water glass was mixed with an aqueous solution of titanium sulfate so that the Si/Ti molar ratio was 1/1, and aqueous ammonia was added to the mixture to form a precipitate. The precipitate was recovered by filtration, washed with water, and subjected to centrifugal dehydration to obtain a dehydrated cake. The cake was air-dried, calcined at 350° C. for 4 hours, transferred to a dessicator, and gradually cooled to obtain a silica/titania catalyst ($SiO_2/TiO_2 = 1/1$).

(Addition Reaction)

A pressure-resistant closed vessel having a capacity of 1 liter and provided with a stirrer was charged with 538 g of a 1-olefin having 16 carbon atoms (Dialene AO-16), and 1.07 g (0.2% by weight based on the olefin) of the thus-obtained silica/titania catalyst was added in the reaction vessel. While stirring in a nitrogen atmosphere, 196 g of maleic acid was added in the reaction vessel, and the mixture was maintained at 170° C. for 30 minutes. Then, the temperature was elevated to 200° C. and the mixture was maintained at this temperature for 6 hours to effect addition reaction.

The reaction product was placed under 15 mmHg at 200° C. to recover the unreacted substances.

The amount of ASA obtained was 624 g, and the ASA was transparent and had a light yellow color. The viscosity was 102 cP as measured at 25° C. Adhesion of a sludge or tar-like product to the inner wall of the reaction vessel was not observed.

COMPARATIVE EXAMPLE 2

Isomerization and the addition reaction were carried out in the same manner as described in Example 2 except that the catalyst was not added.

The unreacted substances were separated from the reaction product in the same manner as described in Example 2. The amount of ASA obtained was 470 g. When floating sludge was removed from this ASA by filtration using filter paper and the viscosity was measured at 25° C., it was found that the viscosity was 158 cP.

The reaction product had a dense brown color, and adhesion of a small amount of a tar-like product to the inner wall of the reaction vessel and the shaft of the stirrer was observed.

EXAMPLE 3

(Preparation of Catalyst)

Water glass and aluminum sulfate were dissolved in water to form a 3% aqueous solution in which the Si/Al molar ratio was 1/1. Then, 10% aqueous ammonia was added to the aqueous solution to form a precipitate. The precipitate was recovered by filtration, washed with water, and subjected to centrifugal separation to obtain a dehydrated cake. The cake was air-dried, calcined at 400° C. for 4 hours and mixed under cooling with powdery magnesium oxide. The mixture was ground in a mortar in a nitrogen current. The silica-alumina/magnesium oxide weight ratio was 10/1. The ground powder was compressed under a pressure of 150 kg/cm² and the compressed body was ground again in a mortar to obtain a silica/alumina/magnesia catalyst.

(Addition Reaction)

A pressure-resistant closed reaction vessel having a capacity of 2 liters and provided with a stirrer was charged with 605 g (3.6 moles) of triisobutylene and 294 g (3 moles) of maleic anhydride, and the inside atmosphere was substituted by nitrogen gas.

Then, 2 g of the silica/alumina/magnesia catalyst prepared above was charged in the reaction vessel and the inner temperature was elevated to 210° C., and the addition reaction was conducted for 8 hours at this temperature. The unreacted substances were removed under a reduced pressure, and 720 g of ASA was obtained.

This ASA had a light yellow color and the viscosity was 250 cP as measured at 25° C.

COMPARATIVE EXAMPLE 3

The addition reaction was carried out in the same manner as described in Example 3 except that the catalyst was not added.

The unreacted substances were removed under a reduced pressure and 612 g of ASA was obtained. Floating sludge was removed from this ASA by filtration using filter paper and the viscosity was measured at 25° C. It was found that the viscosity of the ASA was 2500 cP.

The reaction product was brown, and a large quantity of a tar-like product adhered to the inner wall of the reaction vessel, the gas/liquid interface, the shaft of the stirrer, and the back of the stirring vane.

EXAMPE 4

(Preparation of Catalyst)

Neobeat D (trademark for silica/alumina in which $SiO_2/Al_2O_3$ is 9/1) manufactured and sold by Mizusawa Chem. Ind. was used as the silica/alumina.

The alumina/iron oxide catalyst used was one prepared by filtering and water-washing aluminum hydroxide obtained from aluminum sulfate and aqueous ammonia, adding this aluminum hydroxide to a 20% aqueous solution of iron oxalate so that the Al/Fe molar ratio was 10/1, recovering the formed precipitate by filtration, water-washing the precipitate, air-drying the precipitate, calcining the precipitate at 500° C. for 4 hours, and gradually cooling the calcination product.

The silica/titania/iron oxide catalyst used was one obtained by immersing 100 g of the silica/titania catalyst obtained according to the method described in Example 2 in 100 g of a 20% aqueous solution of iron oxalate, taking out and air-drying the catalyst, calcining the catalyst at 400° C. for 3 hours, and gradually cooling the calcination product.

(ADDITION REACTION )

A heat-resistant closed reaction vessel having a capacity of 2 liters and provided with a stirrer was charged with 500 g of a mixture comprising three 1-olefins having 14, 16, and 18 carbon atoms, respectively, at a molar ratio of 1:1:1, and 1 g (0.2% by weight based on the olefin mixture) of the above-mentioned silica/alumina catalyst was added in the reaction vessel. While stirring was conducted in a nitrogen atmosphere, the mixture was maintained at 200° C. for 3 hours to effect isomerization for changing the positions of double bonds of the 1-olefins and obtain internal olefins.

After the termination of the isomerization, the catalyst used for the isomerization was removed, and the atmosphere in the reaction vessel was substituted by nitrogen gas. Then, 0.5 g of the silica/alumina catalyst, 0.5 g of the alumina/iron oxide catalyst and 0.5 g of the silica/titania/iron oxide catalyst were added afresh to the reaction system, and 220 g (2.24 moles) of maleic anhydride was added.

In the reaction vessel, the temperature was maintained at 190° C. for 10 hours under agitation in a nitrogen atmosphere to conduct addition reaction. After the termination of the reaction, the unreacted substances were removed under a reduced pressure, and 708 g of ASA was obtained. This ASA had a light yellow color and the viscosity was 101 cP as measured at 25° C.

Adhesion of a tar-like product to the inner wall of the reaction vessel or the stirrer was not observed.

COMPARATIVE EXAMPLE 4

Isomerization and addition reaction were carried out in the same manner as described in Example 4 except that the catalysts were not added.

The unreacted substances were removed from the reaction product under a reduced pressure, and 570 g of ASA was obtained. This ASA had a dense brown color and sludge floating in the ASA. After the sludge was removed from the ASA by filtration using filter paper, the viscosity of the ASA was 185 cP as measured at 25° C.

A small amount of a tar-like product adhered to the inner wall of the reaction vessel.

I claim:

1. A process for the preparation of alkenylsuccinic anhydrides, which comprises subjecting an olefin having 2 to 90 carbon atoms and maleic anhydride to addition reaction under heating in the presence of 0.001 to 5% by weight, based on the weight of the olefin, of at least one synthetic solid acid/base catalyst selected from the group consisting of silica/titania, silica/alumina, silica/alumina/titania, silica/alumina/iron oxide, alumina/iron oxide, silica/alumina/magnesia, and silica/titania/iron oxide, the amount of the maleic anhydride being 0.5 to 1.2 moles per mole of the olefin.

2. A process for the preparation of alkenylsuccinic anhydrides according to claim 1, wherein a 1-olefin is used as the olefin.

3. A process for the preparation of alkenylsuccinic anhydrides according to claim 1, wherein an internal olefin formed by isomerizing a 1-olefin is used as the olefin.

4. A process for the preparation of alkenylsuccinic anhydrides according to claim 1, wherein an oligomer of isobutylene isopropylene is used as the olefin.

* * * * *